United States Patent [19]
Ziemann et al.

[11] Patent Number: 4,854,716
[45] Date of Patent: Aug. 8, 1989

[54] DEVICE FOR PROCESSING BONE CEMENT

[75] Inventors: Edeltraud Ziemann, Holz; Andreas Ziemann, Erding, both of Fed. Rep. of Germany

[73] Assignees: Sulzer Brothers Ltd., Winterthur; Allo Pro AG, Baar, both of Switzerland

[21] Appl. No.: 191,389

[22] Filed: May 9, 1988

[30] Foreign Application Priority Data

May 14, 1987 [CH] Switzerland ............ 1852/87

[51] Int. Cl.⁴ ............ B01F 13/06; B01F 7/24
[52] U.S. Cl. ............ 366/139; 366/319; 366/320; 422/225
[58] Field of Search ............ 366/139, 318, 319, 320, 366/321, 322, 323, 324, 79, 80, 81, 83, 84, 85, 87, 88, 89, 90, 20, 245, 247, 248, 249, 251, 241, 348, 349; 422/99, 104, 225

[56] References Cited
U.S. PATENT DOCUMENTS 3,063,813 11/1962 Weinbrenner .............. 366/320
3,113,169 12/1963 O'Brien .............. 422/225
3,366,369 1/1968 Ravasi .............. 366/139
3,640,510 2/1972 Lea .............. 366/139
4,721,390 1/1988 Lidgren .............. 366/139
4,758,096 7/1988 Gunnarsson .............. 366/139

FOREIGN PATENT DOCUMENTS 7612 11/1898 Norway .............. 366/320

Primary Examiner—Robert W. Jenkins
Attorney, Agent, or Firm—Kenyon & Kenyon

[57] ABSTRACT

The device for processing bone cement includes a mixing station with a stirrer for mixing the components of the bone cement under vacuum. The device also includes a resting station in which the mixed ingredients may be stationed for a resting period, processing period and curing period. The temperature-dependent reaction time on the polarmarization reaction can be taken into account in determining the discrete time intervals by means of a temperature sensor for sensing ambient temperature. Acoustic and visual signal generating devices are also provided to indicate the end of each time intervals.

20 Claims, 4 Drawing Sheets

DEVICE FOR PROCESSING BONE CEMENT

This invention relates to a device for processing bone cement. More particularly, this invention relates to a mixing arrangement for mixing bone cement.

Generally, bone cements are manufactured by mixing liquid methylmethacrylate monomer, powdered polymethylmethacrylate and coring agents in a mixing vessel with the components of the resulting dough-like mixture hardening during the curing process. Mixing of the components usually takes place by hand with spatulae and rotating mixers which can also, if necessary, be motor-driven (see for example, F. J. Kummer "Improved Mixing of Bone Cement", page 238 of the Proceedings of the 31st annual ORS, Las Vegas, Nev., USA, from Jan. 21 to 24, 1985). It has also been known to generate and maintain a controlled vacuum in the mixing vessel in order to degassify the mixture as much as possible (see, for example R. L. Wixon et al "Vacuum Mixing of Methylmethacrylate Bone Cements", page 327 of the same Proceedings). When processing low-viscosity cements, which can take place preferentially with a cement gun, a so-called resting period follows completion of the mixing process. During this resting period, polymerization progresses to the point that the dough-like mixture acquires a consistency which permits the mixture to be worked and the rate of monomer loss is reduced. This resting period is followed by a time interval for processing and one for curing the cement.

The bone cements produced in the described manner have proven to be little reproducible in terms of their properties, for example strength or porosity.

Accordingly, it is an object of the invention to be able to mix bone cement in a reproducible manner.

It is another object of the invention to be able to improve the mechanical properties of a cured bone cement.

It is another object of the invention to provide a simple device for the mixing of bone cements to produce uniform properties in the bone cement.

Briefly, the invention provides a device for processing bone cement which includes a mixing arrangement having a mixing container for receiving bone cement ingredients, a stirrer for mixing the ingredients and a motor for driving the stirrer, for example at a low initial feed and a subsequent high speed. In addition, the device includes a vacuum pump means for selectively evacuating the container during mixing of the bone cement ingredients.

The device also includes a control means for controlling the mixing of the ingredients in the container. This control means includes a time counter for monitoring time intervals during mixing as well as signal means, such as audio or visual means, for indicating the end of each time interval. The time counter is also used for monitoring each of a rest period, processing period and curing period following the mixing of the bone cement ingredients with suitable signals being generated at the end of each period by the signal means.

A temperature sensor is also provided for sensing ambient temperature. This sensor is connected to the time counter in order to change the duration of each of the rest period, processing period and curing period as a function of sensed temperature. By controlling the time intervals for the discrete mixing and processing "steps", a bone cement can be obtained which offers improvement and good reproducability of mechanical properties.

Since the time intervals for the rest, processing and curing periods can be controlled as a function of temperature, the chemical reaction time can be directly controlled.

The device also offers the possibility of changing the duration of at least the temperature-dependent time intervals for bone cements of different composition.

In order to facilitate the penetration of the stirrer into the bone cement ingredients, mixing is initially performed at a relatively low stirring speed, for example, of approximately 40 rpm to 100 rpm. Thereafter, the stirring speed can be increased to 120 rpm to 300 rpm. For this purpose, the motor for the stirrer can be resetable from a low to a high stirring speed. Further, the thorough mixing of the bone cement can be improved if the stirring motor can be changed in terms of the direction of rotation, that is, the motor may be reversed.

The quality of the bone cement can be improved considerably, if the mixing of the liquid monomer with the powdered components is carried out in vacuo. For this purpose, a pressure differential of approximately 500 mbar relative to ambient pressure should advisably not be exceeded. Greater pressure differences effect a strong evaporation of the monomer. At significantly lower vacua, however, degassification is insufficient. Thus, a pressure sensor can be connected to the vacuum pump means so that the vacuum is maintained at a constant pressure difference relative to the ambient pressure.

A significant element for good and complete mixing of the components is the stirrer. A construction which has experimentally proven to be particularly effective is one in which the stirrer has a corkscrew shape at least partially filling the mixing container in the axial direction, the outer diameter of which is adapted to the inner diameter of the mixing container, for example which is a cylinder. In order to bring the mixture at the bottom of the cylinder especially in the margin areas back into the mixing process, the stirrer can turn into a horizontal scoop at the free end to encompass the center axis of the cylinder in V-shape. In this process of "bringing back", a mixture column rotating with the stirrer can originate. This is advantageously destroyed again and again by a tearing hook which is attached to the horizontal scoop and directed into the corkscrew.

Further improvements in mixing bone cements can be achieved if the tearing hook extends in the plane parallel to the stirring axis and/or if the tearing hook is directed upward from the horizontal at an angle of at least nearly 60°. Experiments have shown that it is advantageous if the tearing hook ends before the axis-parallel center plane of the stirrer.

Furthermore, possibilities are provided in the device for changing the fully automatic progress of the time intervals, if necessary, through manual input of other time intervals, for example, when testing new cement mixtures. Moreover, apart from the progression of the individual program steps, which in general are indicated acoustically and/or optically, errors in the equipment or unacceptable exceeding of limit values in terms of temperature and/or pressure, which are determined, for example, by the temperature sensor or by the pressure sensor, are also indicated through acoustic and/or optic signals.

These and other objects and advantages of the invention will become more apparent from the following detailed description taken in conjunction with the accompanying drawings wherein.

Figure 1:
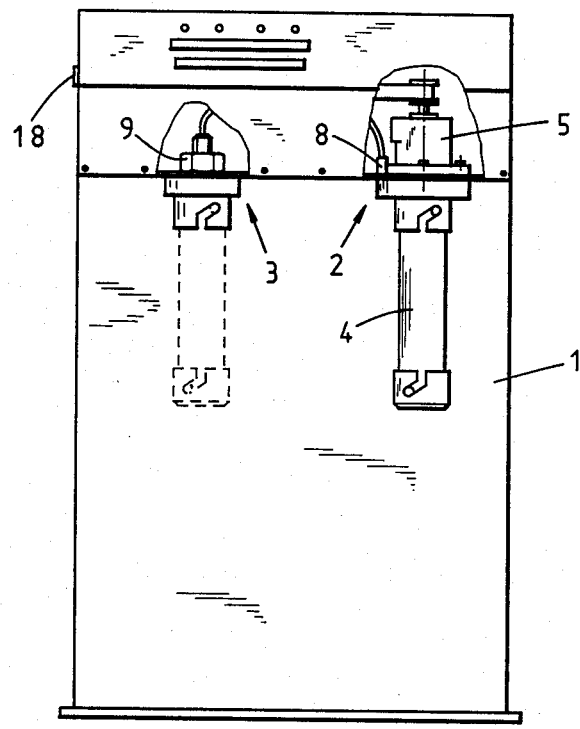
FIG. 1 illustrates a front view a the device constructed in accordance with the invention.
Figure 4:
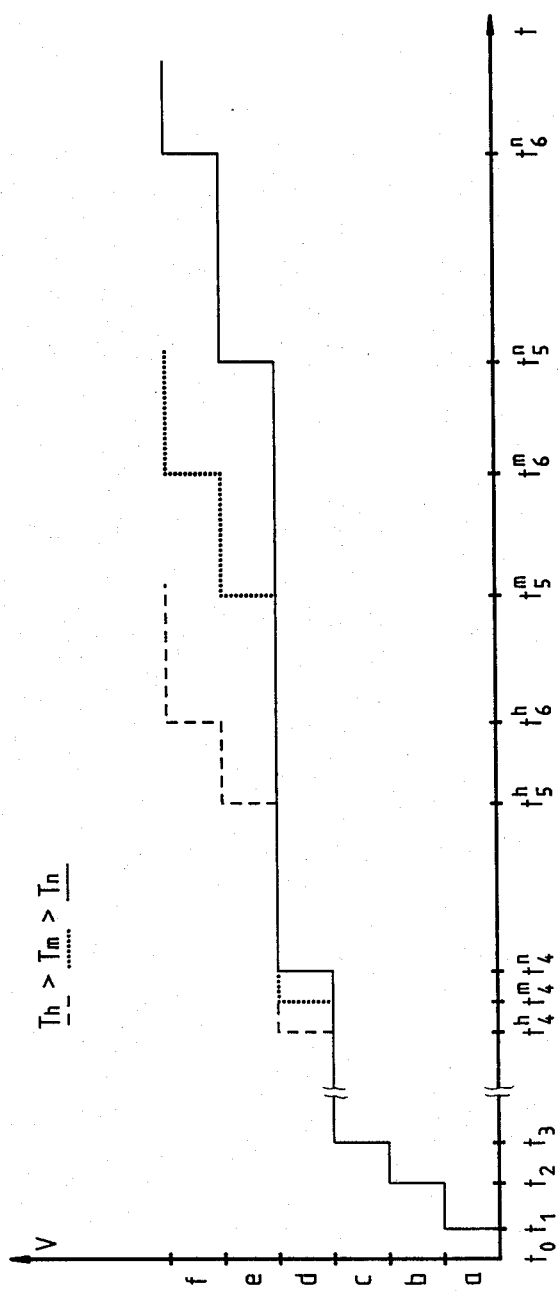
Figure 5:
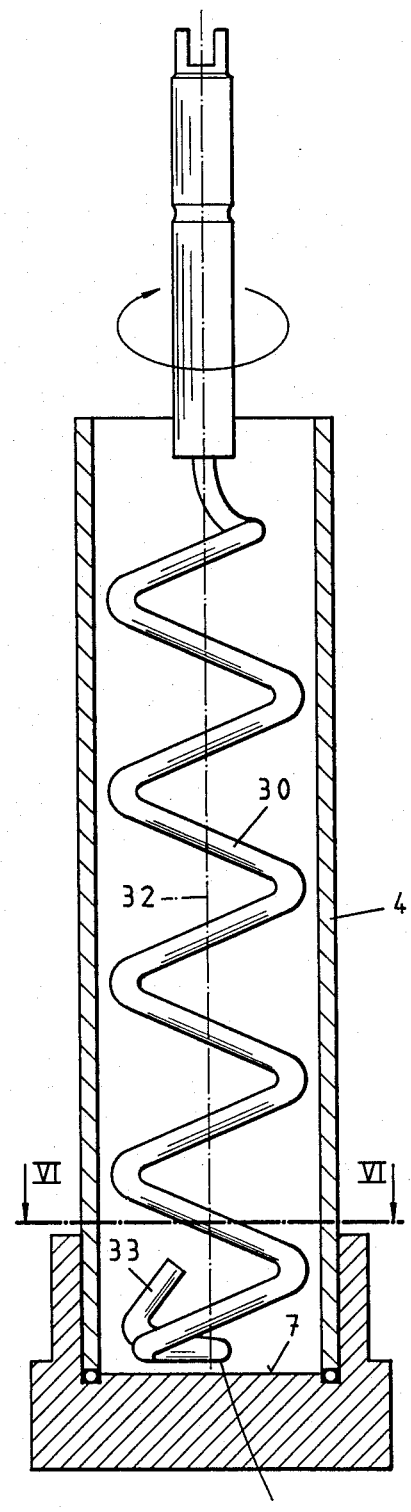
Figure 6:
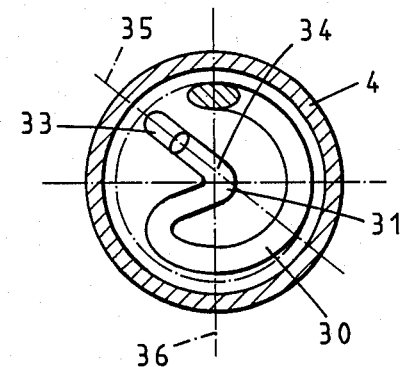

FIG. 4 graphically illustrates a mode of operation of the device of FIG. 1 in accordance with the invention;

FIG. 5 illustrates a part cross sectional view of a mixing arrangement in accordance with the invention; and FIG. 6 illustrates a view taken on line VI—VI of FIG. 5.

Referring to FIG. 1, the device 1 for processing bone cement includes a mixing site or station and a resting site or station 3. Each station 2, 3, is constructed for the removable connection of a container 4, for example in the form of a gun cylinder.

The mixing station 2 includes a depending rotatable stirrer (see FIG. 5) which is driven by a motor 6 (see FIG. 6). This motor 6 can be switched in terms of the direction of rotation and may also have at least two different rotating speeds for one direction of rotation, i.e. a low speed setting, for example, of from 40 to 100 rpm for initial mixing and a high speed setting of, for example 120 to 300 rpm for an actual mixing step.

Figure 3:
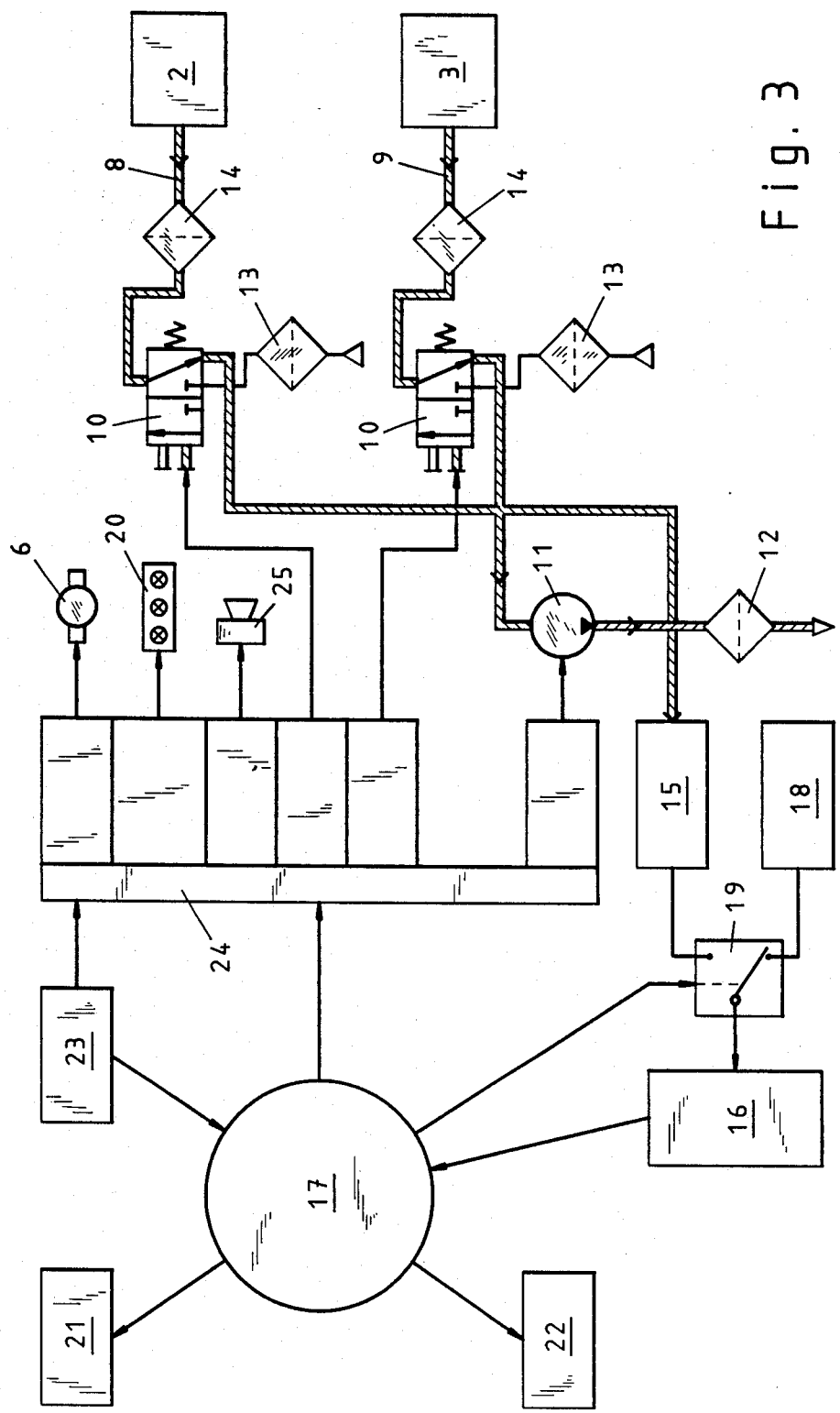
FIG. 3 illustrates a schematic block diagram of the components of the device in FIG. 1.

Referring to FIGS. 1 and 3, each station 2, 3 is provided with a line 8, 9 for connection to a vacuum pump means in the form of a vacuum pump 11. As indicated in FIG. 3, each line 8, 9 passes by way of a separate change-over valve 10 to the vacuum pump 11. Each change-over valve 10 functions to connect either the pump 11 or ambient atmosphere with the container 4 in either station 2, 3. In the one case, the pump 11 generates and maintains a relative vacuum of approximately 500 mbar as compared to the ambient pressure. In the second case, the connection to ambient atmosphere allows the container 4 to be ventilated.

The gases drawn off from the container 4 by the pump 11, which contain a given percentage fraction of evaporated monomer, are blown off through a charcoal filter 12 to the surrounding environment. When the vacuum in the container 4 is abolished, filters 13 for retaining bacteria and germs are provided in the flow paths of the air streaming into the container 4 in order to maintain sterility. Further, the polymer powder drawn in by the vacuum can be retained by the use of coarse filters 14 with 2 $\mu$m pore size.

Referring to FIG. 3, a pressure sensor 15 is provided in the device in order to maintain in the container 4 a vacuum of approximately 500 mbar relative to the ambient atmosphere. In this regard, the pressure sensor 15 emits a measurement signal by way of a measuring site change-over switch 19 and an analog to digital converter 16 to a central control means 17 of the device 1.

Of note, the presence of two stations 2, 3 may be replaced by a single station which serves for mixing and subsequent processing of the bone cement. For example, after the mixing phase, the stirrer (see FIG. 5) may be removed and the motor 6 turned off for the subsequent processing and curing of the bone cement. During the resting phase, the vacuum is switched on again to reduce the porosity of the bone cement and to minimize its toxicity by reducing the toxic monomer phase.

Referring to FIG. 3, the control means 17 may be in the form of a microprocessor which can be purchased on the market and which is used to control all of the steps of the process for processing the bone cement.

A temperature sensor 18 is also provided for sensing ambient temperature. This sensor 18 is connected to the control means 17 via the change-over switch 19 and the converter 16 while being installed, for example in a side wall of the device 1 as indicated in FIG. 1. The measured ambient temperature is also the processing temperature for the bone cement. As is known, this temperature has a significant influence on the time intervals which are available after mixing for the processing "ripeness", the processing itself and the curing of the bone cement.

Figure 2:
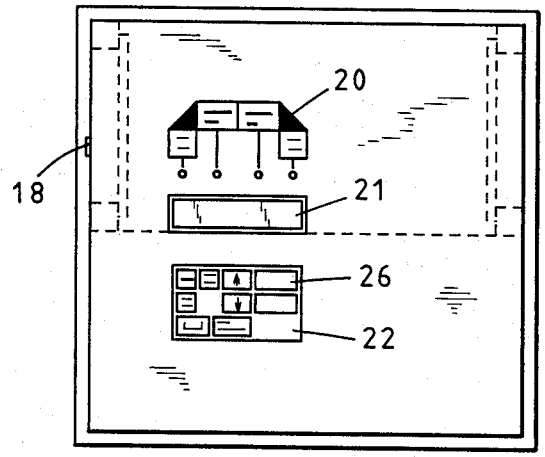
FIG. 2 illustrates a top view of the device or FIG. 1.

The control means 17 is connected to four light emitting diodes 20 (see FIG. 2) which are located on the top side of the device to provide optical signal indications. These diodes 20 indicate the different operating states of the device 1 which are controlled by the control means 17. For example, the diodes 20 indicate the "device on", "automatic program on", "manual program" and "device defect" modes. Further, as indicated in FIG. 2, a two-lined legend field 21 is provided on the top of the device for instructions to the operator during the progression of an automatic or manual program or for the indication of the time remaining for the completion of the individual time intervals.

In addition, an input key panel 22 is provided on the top side of the device 1 which interacts with the control means 17. This key panel 22 includes, for example, a start key 26 and a stop key with which the automatic or manual programs can be started or stopped. A further key permits determination of the time available at a given temperature for the particular cement and the total time required until the cement is cured as well as an indication of this information on the indicator 21. A fourth key visually indicates the given ambient temperature and the rest time necessary at this temperature until the beginning of processing.

A mode key is also provided for selecting of different functions which are initiated with additional keys. Under a mode selection of a "+" ("up arrow") or an "—" ("down arrow") input key and an interrupt key may be activated to permit different selection and function change possibilities.

The interior of the device 1 may be provided with an electronic "beep" element 25 (see FIG. 3) such as an acoustic signal generator which indicates "pre-alerts" before completion of a particular time interval.

As noted above, control of all functions and possibilities of the device 1 takes place through the microprocessor or control means 17 which is supplied by a power supply 23 with electrical energy as is the other energy consuming elements. The supply of the power users is indicated in FIG. 3 by a distributing bus 24 across which the distribution of the control commands of the control mean 17 to the individual function elements takes place.

The signal connections from and to the control means 17 are shown in single continuous lines in FIG. 3 with the signal direction being indicated by arrows.

Referring to FIG. 4, the progression of the processing steps V of an automatic program as a function of time t is diagrammatic illustrated. The operation of the device 1 for a normal mixing and processing process will be explained, with temperature-dependent time progressions shown for a relatively high temperature Th of approximately 24° and a medium temperature Tm of approximately 21°, and a low ambient temperature Tn of approximately 18°. The described bone cement to be mixed is the product known under the name "sulfix" (Trademark of Sulfer Brothers Limited).

After filling the powdered component and the liquid component of the cement into the container 4, the device 1 is put into operation by pressing the start key 26 on the input key pad 22 at time t0. The device 1, in order to adapt its temperature to the room temperature of the operation room, has been set up for a longer period, for example ½ to 1 hour previously. At the mixing station 2 at time t0 only one stirrer 30 (FIG. 5) is attached. When the device 1 is started the stirrer 30, the motor of which initially moves at a slow speed of 60 rpm, rotates slowly in the dough-like mixture of liquid monomer and compact powder component. The stirrer 30 penetrates slowly into the container 4, which is guided upward by the operator of the device 1 and connected to the mixing station 2. This step is labeled a in FIG. 4.

After completion of a time interval of approximately 15 seconds at time t1, the slow running initial mixing is completed. At this time, the control means 17 automatically puts out a signal, which switches the stirring motor 6 from 60 rpm to the normal higher stirring speed of 180 rpm (step b). After the stirrer 30 has mixed both components at full stirring speed for a given time, the vacuum pump 11 is set into operation at time t2 by control means 17. Operation of the pump is monitored by the sensor 15 and controlled in such a way, that the negative pressure relative to the ambient pressure is approximately 500 mbar and does not exceed this value. Greater pressure differences lead, as already mentioned, to an unacceptable high evaporation of the liquid monomer, while lesser negative pressures impair the degassification of the mixture and prevent optimum degassification. The degassification of container 4, forming step c, during mixing lasts until time t3. When this is reached, the vacuum pump 11 is automatically turned off and the mixing station 2 ventilated in that the appropriate valve 10 is switched over under the control of means 17.

An acoustic signal and a corresponding command indication on the indicator element and the legend field 21, at time t3, furthermore, demand that the container 4 be detached from the mixing station 2 and transferred to the resting station 3. Once this has taken place, the vacuum pump 11 is again set into operation by pressing the starting key 26. Simultaneously, the waiting time or rest time, which is a function of the temperature and the cement mixture which must or may elapse until optimum workability of the cement is achieved is indicated in minutes and seconds and monitored by backward counting. This waiting or resting time t4 indicated in step d of FIG. 4 is apart from the running indication of the backward counter, acoustically and optically indicated by the beep element 25, for example, by blinking of the light emitting diode for the indication "program running". Since the waiting or resting time is a function of temperature, three different times t4h, t4m, and t4n obtain in FIG. 4 for a relatively high (Th), an average (Tm), and a low ambient temperature (Tn).

This ambient temperature is detected in a range of, for example, 18° to 24° by the sensor 18 which influences the time counter in the program of control means 17 accordingly.

Pushing the starting key 26 at the particular time t4, causes abolishment of the vacuum at the resting station 3 (and in the container 4) container 4 can then be removed for processing. Simultaneously, the indication "time to press in" appears on the legend field 21 with the associated time interval—again temperature-dependent—for processing the cement again being monitored by backward counting.

In a manner similar to the end of the resting times, the processing times completed at times t5 (step e) are optically and acoustically indicated. With the signals for the end of the processing time, the indication and count of the curing times (step f) starts automatically, which again are ended—depending on temperature—at time t6 for the different temperatures. This is also indicated acoustically by a signal and by an indication in the legend field 21. At the end of the curing time, the device 1 is automatically turned off.

As already indicated, the shape of the stirrer 30 (FIG. 5) for perfect mixing and for good and reproducible thorough mixing of both components is of considerable importance. Experimentally, a stirrer shape has proven particularly suitable in which the stirrer 30 penetrates the axial length of the container or the gun cylinder 4 and its diameter reaches as closely to the wall of the cylinder 4 as possible without actually touching it. The free end of the stirrer 30 initially forms a horizontal scoop 31, which in the form of a V (FIG. 6) encompasses the longitudinal axis 32 of the stirrer 30 and extends near the floor 7 of the container 4.

The scoop 31 changes over into a tearing hook 33, which extends at least nearly in a plane 35 parallel to the longitudinal axis of the stirrer 30, which plane is defined by the tearing hook itself and one arm 34 of the scoop 31. The tearing hook 33 forms with the horizontal floor 7 approximately an angle of 60° and ends in front of the axis-parallel center plane 36 of the stirrer 30.

The scoop 31 has a shovel effect and permits picking up the bone cement in margin zones of the container to move the bone cement into the upper region of the container 4. The thereby generated but undesirable formation of a homogeneous rotating cement column is prevented again and again by the tearing hook 33 from rotating with the stirrer 30 at the same speed because the tearing hook 33 prevents a caking together of the bone cement to form this compact column. By the fact that the hook 33 runs eccentrically, a column in the process of formation is again and again torn apart, which permits homogenous mixing of the entire bone cement.

The invention thus provides a device for the processing of bone cement which is able to reproduce bone cements having the same or similar characteristics.

Further, the invention provides a mixing arrangement for automatically mixing bone cement ingredients.

The invention further provides a device for the mixing of bone cement ingredients which is independent of individual influences of the mixing personnel.

The invention further permits bone cement mixtures to be obtained which have great strength and low porosity and which contain a minimized amount of toxical monomer.

What is claimed is:

1. A device for processing bone cement comprising
   a mixing arrangement including a mixing container for receiving bone cement ingredients, a stirrer for mixing the ingredients, and a motor for driving said stirrer;
   a vacuum pump for selectively evacuating said container; and
   a control means connected to said motor and said pump for controlling mixing of the ingredients in said container, said means including a time counter for monitoring time intervals during mixing and signal means for indicating the end of each said time interval.

2. A device as set forth in claim 1 which further comprises a temperature sensor for sensing ambient temperature connected to said control means for changing the duration of at least some of said time intervals as a function of sensed temperature.

3. A device as set forth in claim 2 wherein said control means includes means for adjusting said time intervals in dependence on the ingredients for the bone cement.

4. A device as set forth in claim 1 wherein said motor is adjustable in speed.

5. A device as set forth in claim 1 wherein said motor is reversible.

6. A device as set forth in claim 1 which further comprises a pressure sensor connected to said vacuum pump to maintain a constant pressure differential relative to ambient pressure during discrete time intervals.

7. A device as set forth in claim 1 wherein said stirrer is of corkscrew shape having an outer diameter slightly less than an inner diameter of said container.

8. A device as set forth in claim 7 wherein said stirrer has a horizontally disposed scoop of V-shape encompassing a longitudinal axis of said stirrer and a tearing hook extending from said scoop towards said axis.

9. A device as set forth in claim 8 wherein said hook is disposed in a vertical plane parallel to said axis.

10. A device as set forth in claim 8 wherein said hook defines an angle of 60° with a horizontal plane perpendicular to said axis.

11. A device as set forth in claim 8 wherein said hook terminates at a point spaced from said axis.

12. A device as set forth in claim 1 wherein said control means includes a temperature sensor for sensing ambient temperature connected to said control means for changing the duration of at least some of said time intervals as a function of sensed temperature and a pressure sensor connected to said vacuum pump to maintain a constant pressure differential relative to ambient pressure during discrete time intervals.

13. A mixing arrangement for bone cement including
a container for receiving bone cement ingredients; and
a rotatable stirrer for mixing the ingredients in said container, said stirrer having a corkscrew shape with a horizontally disposed scoop of V-shape encompassing a longitudinal axis of said stirrer and a tearing hook extending from said scoop towards said axis.

14. A mixing arrangement as set forth in claim 13 which further comprises a vacuum pump for selectively evacuating said container during mixing of the bone cement ingredients.

15. A stirrer for mixing bone cement having a corkscrew shape extending along a longitudinal axis, a V-shaped scoop at one end extending perpendicularly of said axis and a tearing hook extending from said scoop towards said axis.

16. A stirrer as set forth in claim 15 wherein said hook is disposed in a plane parallel to said axis.

17. A stirrer as set forth in claim 15 wherein said hook defines an angle of 60° with a horizontal plane perpendicular to said axis.

18. A device for mixing bone cement comprising
a mixing station including a rotatable stirrer for receiving a container having mixable bone cement ingredients therein;
a vacuum pump means connected to said mixing station for maintaining a predetermined negative pressure in the container during mixing of the bone cement ingredients; and
a resting station for receiving the container after mixing, said resting station being in selective communication with said vacuum pump means for evacuation of the container during curing of the bone cement.

19. A device as set forth in claim 18 which further comprises a control means connected to said stirrer and said pump for sequentially operating said stirrer and pump to mix the bone cement ingredients and degassify the mixture under a negative pressure of approximately 500 mbar for a predetermined time interval.

20. A device as set forth in claim 19 wherein said control means includes a time counter for monitoring each of a rest period, processing period and curing period after said time interval and a temperature sensor for sensing ambient temperatures connected to said time counter for changing the duration of each of said periods as a function of sensed temperature.

* * * * *

UNITED STATES PATENT AND TRADEMARK OFFICE
CERTIFICATE OF CORRECTION

PATENT NO. : 4,854,716

DATED : Aug. 8, 1989

INVENTOR(S) : EDELTRAUD ZIEMANN, et al

It is certified that error appears in the above-identified patent and that said Letters Patent is hereby corrected as shown below:

```
Column 3, line 5  "or" should be -of-
Column 4, line 56 "mean" should be -means-
Column 4, line 63 "diagrammatic" should be -diagrammatically-
Column 4, line 67 "24°" should be -24°c.-
Column 4, line 68 "21°" should be -21°c.-
Column 5, line 1  "18°" should be -18°c.-
Column 5, line 62 "18° to 24°" should be -18°c to 24°c-
Column 6, line 9  "starts" should be -start-
```

Signed and Sealed this

Sixteenth Day of October, 1990

Attest:

HARRY F. MANBECK, JR.

*Attesting Officer*    *Commissioner of Patents and Trademarks*

UNITED STATES PATENT AND TRADEMARK OFFICE
CERTIFICATE OF CORRECTION

PATENT NO. : 4,854,716

DATED : August 8, 1989

INVENTOR(S) : EDELTRAUD ZIEMANN, et al

It is certified that error appears in the above-identified patent and that said Letters Patent is hereby corrected as shown below:

In the Title Page under [73] Assignees change "SULZER ... Switzerland: to -ALLO PRO AG, Baar, Switzerland- Signed and Sealed this Seventh Day of April, 1992

Attest:

HARRY F. MANBECK, JR.

*Attesting Officer*  *Commissioner of Patents and Trademarks*